US008343085B2

(12) United States Patent
Toyoda et al.

(10) Patent No.: US 8,343,085 B2
(45) Date of Patent: Jan. 1, 2013

(54) BLOOD PURIFICATION APPARATUS AND PRIMING METHOD THEREOF

(75) Inventors: Masahiro Toyoda, Shizuoka (JP); Satoshi Takeuchi, Shizuoka (JP)

(73) Assignee: Nikkiso Co., Ltd., Tokyo (JP)

( * ) Notice: Subject to any disclaimer, the term of this patent is extended or adjusted under 35 U.S.C. 154(b) by 482 days.

(21) Appl. No.: 12/680,298

(22) PCT Filed: Dec. 15, 2009

(86) PCT No.: PCT/JP2009/006897
§ 371 (c)(1),
(2), (4) Date: Mar. 26, 2010

(87) PCT Pub. No.: WO2010/070886
PCT Pub. Date: Jun. 24, 2010

(65) Prior Publication Data
US 2011/0213289 A1    Sep. 1, 2011

(30) Foreign Application Priority Data

Dec. 16, 2008  (JP) ................................. 2008-319196
Apr. 28, 2009  (JP) ................................. 2009-108582
May 25, 2009  (JP) ................................. 2009-124931

(51) Int. Cl.
*A61M 37/00*    (2006.01)

(52) U.S. Cl. .......... 604/6.06; 210/646; 210/767
(58) Field of Classification Search .............. 604/4.01, 604/5.01, 6.06–6.11, 6.15, 6.16; 210/645–647, 210/767
See application file for complete search history.

(56) References Cited

FOREIGN PATENT DOCUMENTS

JP    2000-093449 A    4/2000
WO    2006073166 A1    7/2006

OTHER PUBLICATIONS

English translation of abstract and spec. of JP 2000-093449 A to Miyatake et al.*

* cited by examiner

*Primary Examiner* — Melanie Hand
(74) *Attorney, Agent, or Firm* — McDermott Will & Emery LLP

(57) ABSTRACT

The present invention relates to a blood purification apparatus for extracorporeally circulating the blood of a patient so as to purify the blood for medical treatment incorporating a dialyzer and a method for priming the blood purification apparatus, wherein the present invention provides a blood purification apparatus and its priming method which can simply and easily automate the priming operation and also can surely and smoothly perform the bubble purging of the dialyzer.

16 Claims, 14 Drawing Sheets

BLOOD PURIFICATION APPARATUS AND PRIMING METHOD THEREOF

CROSS-REFERENCE TO RELATED APPLICATIONS

The present application is the United States national phase application under 35 U.S.C. §371 of Patent Cooperation Treaty Application No. PCT/JP2009/006897, filed on Dec. 15, 2009, which claims the benefit of Japanese Application Nos. 2008-319196, filed on Dec. 16, 2008, 2009-108582, filed on Apr. 28, 2009, and 2009-124931, filed on May 25, 2009. The contents of these applications are incorporated by reference herein in their entireties.

FIELD OF THE INVENTION

The present invention relates to a blood purification apparatus for extracorporeally circulating blood of a patient to purify the blood used e.g. in the dialysis treatment using a dialyzer and a method for priming the blood purification apparatus.

BACKGROUND OF THE INVENTION

In general, it is used in the dialysis treatment a blood circuit for extracorporeally circulating the blood of a patient and returning it again into a body of a patient. The blood circuits mainly comprises an arterial blood circuit and a venous blood circuit adapted to be connected to a dialyzer (blood purification means) provided e.g. with hollow fiber membranes. An arterial puncture needle and a venous puncture needle can be mounted on tips respectively of the arterial blood circuit and the venous blood circuit and thus the extracorporeal circulation of the blood can be performed in the dialysis treatment with the puncture needles being punctured to a body of a patient.

A peristaltic blood pump is arranged in the arterial blood circuit and the blood of a patient is adapted to be fed to the dialyzer by driving the blood pump. On the other hand an arterial drip chamber and a venous drip chamber are connected to the arterial blood circuit and the venous blood circuit respectively and thus the blood is returned to a body of a patient after removal of bubbles therefrom.

A priming solution supplying line (physiological saline solution line) is connected to the arterial blood circuit at the upstream side (i.e. arterial puncture needle side) of the blood pump via a T-joint for supplying the physiological saline solution during the priming and the autotransfusion. The dialyzer is structured so that the priming is performed before the dialysis treatment by supplying the physiological saline solution and charging the structural elements such as blood circuits and drip chambers connected thereto with the physiological saline solution and then the physiological saline solution is replaced with blood remained in the blood circuits after the dialysis treatment and finally the remained blood is returned to a patient for performing the autotransfusion. A dialysis apparatus furnished with the priming solution supplying line is disclosed e.g. in Japanese Laid-open Patent Publication No. 2000-93449 ("the '449 Publication").

In particular the priming operation will be concretely described with reference to FIGS. 14 and 15. A reference numeral 103 denotes a dialyzer functioning as a blood purification means in which a blood flow route for passing blood of a patient therethrough and a dialysate flow route for passing dialysate therethrough. The blood flow route has on its opposite ends a blood inlet port "a" for introducing the blood to be connected to a arterial blood circuit 101 on which a blood pump 104 is arranged and a blood outlet port "b" for discharging the blood to be connected to a venous blood circuit 102. On the other hand the dialysate flow route has on its opposite ends a dialysate inlet port "c" for introducing the dialysate to be connected to a dialysate introducing line 107 and a dialysate outlet port "d" for discharging the dialysate to be connected to a dialysate discharging line 108.

Prior to the dialysis treatment physiological saline solution (priming solution) in a physiological saline solution bag 105 is supplied to the arterial blood circuit 101 via a priming solution supplying line 106 by driving the blood pump 104. In this time the dialyzer 103 is arranged so that the blood outlet port "b" is positioned upward and the blood flow route within the dialyzer 103 and the blood circuit are charged with the physiological saline solution by discharging the physiological saline solution introduced into the dialyzer 103 from the blood outlet port "b" through the blood flow route (see FIG. 14).

Then the dialyzer 103 is arranged upside down with clamping the priming solution supplying line 106 so that the blood inlet port "a" is positioned upward (see FIG. 15). Then after having introduced the dialysate from the dialysate introducing line 107 and passed through the dialysate flow route within the dialyzer 103, the dialysate flow route is charged with the dialysate by discharging the dialysate from the dialysate discharging line 108. Thus the priming of the dialysate flow route has been completed following the priming of the blood flow route.

In usual bubbles in the blood flow route moves upward during the priming operation and thus it is necessary to perform the bubble purging by leading the bubbles toward the venous blood circuit 102 with positioning the blood outlet port "b" upward. On the contrary if the priming would be performed under such a condition (i.e. condition of the blood outlet port "b" positioned upward), the dialysate flows from the top to the bottom of the dialyzer 103 against the moving direction of the bubbles. Accordingly the dialyzer 103 has been arranged upside down so that the dialysate can flow from the bottom to the top of the dialyzer 103 to achieve smooth motion of the bubbles and thus more positive bubble purging.

However, such a priming method has a problem of requiring a long priming duration because of increase of priming operation steps due to requirement of arranging the dialyzer 103 upside down before performing the priming of the dialysate flow route and after the priming of the blood flow route. In addition extension of the priming time (duration) causes other problems of delay of commence of dialysis treatment and thus of increase of burden both for a patient and medical personnel.

For solving these problems there has been proposed a technology e.g. as disclosed in PCT International Publication laid opened under No. WO2006/073166 ("the '166 publication"). In this priming technology, following steps are sequentially performed: an initial introducing step in which a tip of an arterial blood circuit and a tip of a venous blood circuit are connected each other and then the venous blood circuit is charged with priming solution (physiological saline solution) by feeding the priming solution by its own weight, a overflowing step in which the priming solution is introduced into the arterial blood circuit in the normal direction by driving a blood pump in the normal direction and discharged from an overflow line extending from a drip chamber arranged on the venous blood circuit, and a reversely recirculating treatment step in which the priming solution is flowed in a direction reverse to that in the overflowing step by driving the blood pump in the reverse direction. According to the priming method of the prior art it is possible to perform the priming operation with keeping the condition in which the blood inlet port of the dialyzer is positioned upward and to simplify the priming operation and thus to easily achieve an automated priming operation.

SUMMARY OF THE INVENTION

However in the blood purification apparatus of the prior art, although it is possible to carry out the priming operation with keeping the condition in which the blood inlet port of the dialyzer is positioned upward, it is afraid that the bubbles would be dwelled in the blood flow route in the dialyzer because of the priming solution flowing from the blood inlet port to the blood outlet port (from the top to the bottom of the blood flow route). Although it is supposed that almost dwelled bubbles will be forced upward in the reversely recirculating treatment step in which the priming solution is flowed from the blood outlet port to the blood inlet, since a large amount and high flowing speed of the priming solution are required to purge the once dwelled bubbles, there is also a problem of requiring long priming time.

It is, therefore, an object of the present invention to provide a blood purification apparatus and its priming method which can simply and easily automate the priming operation and also can surely and smoothly perform the bubble purging of the blood purification means (dialyzer).

For achieving the object of the present invention, there is provided according to the present invention of claim 1 a blood purification apparatus comprising a blood circuit including an arterial blood circuit and a venous blood circuit for extracorporeally circulating the blood of a patient from a tip of the arterial blood circuit to a tip of the venous blood circuit; a blood purification means for purifying the blood of a patient flowing through the blood circuit interposed between the arterial blood circuit and the venous blood circuit of the blood circuit and formed with a blood flow route through which the blood of a patient flows and a dialysate flow route through which dialysate flows via blood purification membranes arranged therebetween; a blood pump arranged in the arterial blood circuit; a dialysate introducing line and a dialysate discharging line connected respectively to an inlet port and an outlet port of the dialysate flow route of the blood purification means; a priming solution supplying line connected to the arterial blood circuit for supplying priming solution to the blood circuit; a blood inlet port and a blood outlet port arranged at opposite ends of the blood purification means, the blood inlet port being connected to the arterial blood circuit for introducing the blood therefrom into the blood flow route within the blood purification means and the blood outlet port being connected to the venous blood circuit for discharging the blood from the blood flow route within the blood purification means; a dialysate inlet port and a dialysate outlet port arranged at the side of the blood purification means, the dialysate inlet port being connected to the dialysate introducing line for introducing the dialysate therefrom into the dialysate flow route within the blood purification means and the dialysate outlet port being connected to the dialysate discharging line for discharging the dialysate from the dialysate flow route within the blood purification means; a drip chamber connected to the venous blood circuit; an overflow line extending from an air layer side of the drip chamber for discharging overflowed solution from the drip chamber; a valve means being able to arbitrarily open and close the overflow line; a venous bubble detecting means arranged at a predetermined portion near the tip of the venous blood circuit for detecting bubbles in the solution flowing through the predetermined portion; and a closed circulation circuit being able to be formed by connecting the tip of the arterial blood circuit and the tip of the venous blood circuit when performing the priming operation before the dialysis treatment characterized in that the blood purification apparatus further comprises a control means being able to control the blood pump and the valve means with receiving detecting signals from the venous bubble detecting means; and that during the priming operation the control means can sequentially control following steps under a condition in which the blood inlet port of the blood purification means is set at a top position: an overflowing step in which the priming solution is supplied to the drip chamber from the priming solution supplying line via the venous blood circuit and then discharged through the over flow line by stopping the blood pump and opening the valve means; a circulating step in which the priming solution is supplied to the arterial blood circuit from the priming solution supplying line via the venous blood circuit and the blood purification means by driving the blood pump in reverse and closing the valve means; and a shifting step for shifting the circulating step to the overflowing step so long as the venous bubble detecting means detects bubbles.

The invention of claim 2 is a blood purification apparatus of claim 1 characterized in that the control means controls to perform repeat of the overflowing step and the circulating step until any bubble cannot be detected by the venous bubble detecting means.

The invention of claim 3 is a blood purification apparatus of claim 1 or 2 characterized in that a drip chamber for the priming solution is arranged on the priming solution supplying line, and that the control means controls to perform a priming solution pool forming step for forming a priming solution pool within the drip chamber for the priming solution before a first overflowing step.

The invention of claim 4 is a blood purification apparatus of any one of claims 1~3 characterized in that the control means controls during the priming operation before the first overflowing step to perform a dialysate charging step in which the dialysate introducing line and the dialysate discharging line are connected respectively to the dialysate inlet port and the dialysate outlet port to pass the dialysate through the dialysate flow route within the blood purification means and to fill it with the dialysate.

The invention of claim 5 is a blood purification apparatus of any one of claims 1~4 characterized in that the control means controls during the circulating step to reduce the pressure in the dialysate flow route within the blood purification means.

The invention of claim 6 is a blood purification apparatus of claim 5 characterized in that it further includes an ultrafiltration pump for ultrafiltrating the blood of a patient flowing in blood purification means, and that the pressure in the dialysate flow route within the blood purification means is reduced by driving the ultrafiltration pump.

The invention of claim 7 is a blood purification apparatus of any one of claims 1~6 characterized in that the control means controls after the overflowing step and before the circulating step to perform the normal rotation of the blood pump.

The invention of claim 8 is a blood purification apparatus of any one of claims 1~7 characterized in that the control means controls during the circulating step to perform supply of the dialysate to the dialysate flow route within the blood purification means while supplying of the priming solution to the blood flow route within the blood purification means.

The invention of claim 9 is a method for priming a blood purification apparatus comprising a blood circuit including an arterial blood circuit and a venous blood circuit for extracorporeally circulating the blood of a patient from a tip of the arterial blood circuit to a tip of the venous blood circuit; a blood purification means for purifying the blood of a patient flowing through the blood circuit interposed between the arterial blood circuit and the venous blood circuit of the blood circuit and formed with a blood flow route through which the blood of a patient flows and a dialysate flow route through which dialysate flows via blood purification membranes arranged therebetween; a blood pump arranged in the arterial blood circuit; a dialysate introducing line and a dialysate discharging line connected respectively to an inlet port and an outlet port of the dialysate flow route of the blood purification means; a priming solution supplying line connected to the arterial blood circuit for supplying priming solution to the blood circuit; a blood inlet port and a blood outlet port arranged at opposite ends of the blood purification means, the blood inlet port being connected to the arterial blood circuit for introducing the blood therefrom into the blood flow route within the blood purification means and the blood outlet port being connected to the venous blood circuit for discharging the blood from the blood flow route within the blood purification means; a dialysate inlet port and a dialysate outlet port arranged at the side of the blood purification means, the dialysate inlet port being connected to the dialysate introducing line for introducing the dialysate therefrom into the dialysate flow route within the blood purification means and the dialysate outlet port being connected to the dialysate discharging line for discharging the dialysate from the dialysate flow route within the blood purification means; a drip chamber connected to the venous blood circuit; an overflow line extending from an air layer side of the drip chamber for discharging overflowed solution from the drip chamber; a valve means being able to arbitrarily open and close the overflow line; a venous bubble detecting means arranged at a predetermined portion near the tip of the venous blood circuit for detecting bubbles in the solution flowing through the predetermined portion; and a closed circulation circuit being able to be formed by connecting the tip of the arterial blood circuit and the tip of the venous blood circuit when performing the priming operation before the dialysis treatment characterized in that following steps are sequentially performed during the priming operation under a condition in which the blood inlet port of the blood purification means is set at a top position: an overflowing step in which the priming solution is supplied to the drip chamber from the priming solution supplying line via the venous blood circuit and then discharged through the over flow line by stopping the blood pump and opening the valve means; a circulating step in which the priming solution is supplied to the arterial blood circuit from the priming solution supplying line via the venous blood circuit and the blood purification means by driving the blood pump in reverse and closing the valve means; and a shifting step for shifting the circulating step to the overflowing step so long as the venous bubble detecting means detects bubbles.

The invention of claim 10 is a method for priming a blood purification apparatus of claim 9 characterized in that the overflowing step and the circulating step are repeated until any bubble cannot be detected by the venous bubble detecting means.

The invention of claim 11 is a method for priming a blood purification apparatus of claim 9 or 10 characterized in that a drip chamber for the priming solution is arranged on the priming solution supplying line, and that a priming solution pool forming step for forming a priming solution pool within the drip chamber for the priming solution is performed before a first overflowing step.

The invention of claim 12 is a method for priming a blood purification apparatus of any one of claims 9~11 characterized in that during the priming operation before the first overflowing step it is performed a dialysate charging step in which the dialysate introducing line and the dialysate discharging line are connected respectively to the dialysate inlet port and the dialysate outlet port to pass the dialysate through the dialysate flow route within the blood purification means and to fill it with the dialysate.

The invention of claim 13 is a method for priming a blood purification apparatus of any one of claims 9~12 characterized in that the pressure in the dialysate flow route within the blood purification means is reduced during the circulating step.

The invention of claim 14 is a method for priming a blood purification apparatus of claim 13 characterized in that it further includes an ultrafiltration pump for ultrafiltrating the blood of a patient flowing in blood purification means, and that the pressure in the dialysate flow route within the blood purification means is reduced by driving the ultrafiltration pump.

The invention of claim 15 is a method for priming a blood purification apparatus of any one of claims 9~14 characterized in that the blood pump is driven as the normal rotation after the overflowing step and before the circulating step.

The invention of claim 16 is a method for priming a blood purification apparatus of any one of claims 9~15 characterized in that the dialysate is supplied to the dialysate flow route within the blood purification means while the priming solution is supplied to the blood flow route within the blood purification means during the circulating step.

EFFECTS OF THE INVENTION

According to the inventions of claims 1 and 9, since the overflowing step and the circulating step are sequentially performed under a condition in which the blood inlet port of the blood purification means is set at a top position and the circulating step is shifted to the overflowing step so long as the venous bubble detecting means detects bubbles, it is possible to simply and easily automate the priming operation and also to surely and smoothly perform the bubble purging of the blood purification means.

According to the inventions of claims 2 and 10, since the overflowing step and the circulating step are repeated until any bubble cannot be detected by the venous bubble detecting means, it is possible to more positively discharge the bubbles in the blood circuit during the priming operation.

According to the inventions of claims 3 and 11, since the priming solution pool forming step for forming a priming solution pool within the drip chamber for the priming solution is performed before a first overflowing step, it is possible to form a priming solution pool in the drip chamber for the priming solution during the priming operation.

According to the inventions of claims 4 and 12, since during the priming operation before the first overflowing step it is performed a dialysate charging step in which the dialysate introducing line and the dialysate discharging line are connected respectively to the dialysate inlet port and the dialysate outlet port to pass the dialysate through the dialysate flow route within the blood purification means and to fill it with the dialysate, it is possible to avoid generation of bubbles in the priming solution due to moving of air in the dialysate flow route into the blood flow route via the blood purification membrane during the overflowing step or the circulating step which are performed thereafter.

In addition, the inventions of claims 4 and 12 can be advantageously applied to a so-called a plate type blood purification means comprising a plurality of laminated sheet filtrating membranes. Furthermore when the inventions of claims 4 and 12 are applied to a so-called wet type blood filtrating means in which charging solution has been previously charged, it is possible to avoid the charging solution in the dialysate flow route from being moved into the blood flow route via the blood purification membrane and mingled with the priming solution.

According to the inventions of claims 5 and 13, since the pressure in the dialysate flow route within the blood purification means is reduced during the circulating step, it is possible to surely keep a volume of the blood flow route and thus to obtain smooth flowing of priming solution in the blood flow route. Especially when the inventions of claims 5 and 13 are applied to a so-called plate type blood purification means, it is possible to surely keep the volume of the blood flow route by expanding the blood flow route between the sheet-shaped filtrating membranes.

According to the inventions of claims 6 and 14, since the pressure in the dialysate flow route within the blood purification means is reduced by driving the ultrafiltration pump, no separate means is required for reducing pressure in the dialysate flow route.

According to the inventions of claims 7 and 15, since the blood pump is driven as the normal rotation after the overflowing step and before the circulating step, it is possible to remove bubbles in a flow route between the blood outlet port of the blood purification means on the venous blood circuit to the drip chamber before the circulating step and thus to perform the priming operation more smoothly and in short time.

According to the inventions of claims 8 and 16, since the dialysate is supplied to the dialysate flow route within the blood purification means while the priming solution is supplied to the blood flow route within the blood purification means during the circulating step, it is possible to more positively avoid entering of bubbles from the dialysate flow route to the blood flow route even if using a dialyzer excellent both in the solute removing ability and the permeability and thus to perform the priming with using substantially same amount of priming solution as that used in a normal dialyzer.

MODES FOR CARRYING OUT THE INVENTION

Preferable embodiments of the present invention will be hereinafter described with reference to the drawings.

Figure 1:
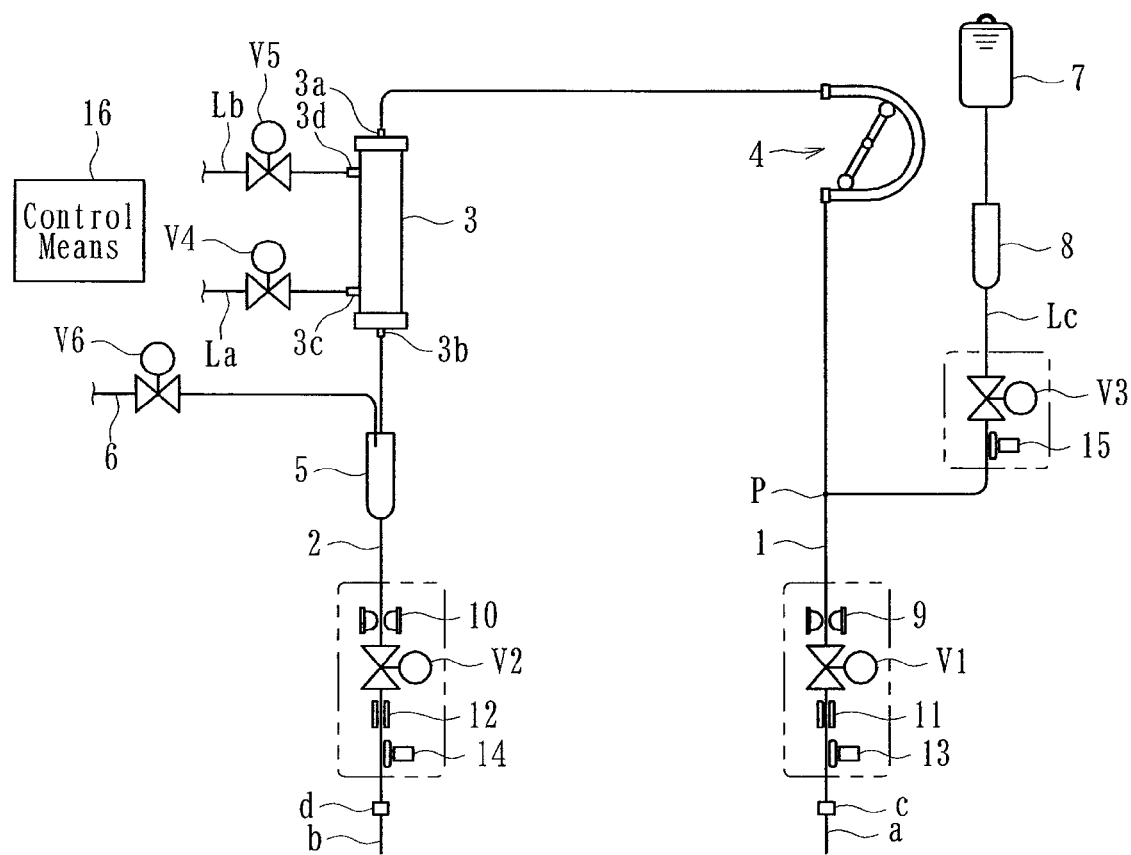
[FIG. 1] A schematic view showing a dialysis apparatus (blood purification apparatus) of a preferred embodiment of the present invention.

A blood purification apparatus of a preferred embodiment of the present invention is a dialysis apparatus for performing dialysis treatment and comprises, as shown in FIG. 1, blood circuits including an arterial blood circuit 1 and a venous blood circuit 2, a dialyzer (blood purification means) 3 interposed between the arterial blood circuit 1 and the venous blood circuit 2 for purifying blood flowing the blood circuits, a peristaltic blood pump 4 arranged on the arterial blood circuit 1, a drip chamber 5 connected to the venous blood circuit 2, a priming solution containing means 7 for containing physiological saline solution as priming solution, a priming solution supplying line Lc for connecting the priming solution containing means 7 and the arterial blood circuit 1, and a drip chamber 8 for the priming solution arranged on the priming solution supplying line Lc.

An arterial puncture needle "a" is adapted to be connected to a tip of the arterial blood circuit 1 via a connector "c" and the peristaltic blood pump 4 is arranged on the arterial blood circuit 1. On the other hand, in the venous blood circuit 2, a venous puncture needle "b" is adapted to be connected to a tip of the venous blood circuit 2 via a connector "d" and a drip chamber 5 is arranged on the venous blood circuit 2. When starting the blood pump 4 after having punctured the arterial puncture needle "a" and the venous puncture needle "b" respectively into the artery and the vein of a patient, blood of a patient flows through the arterial blood circuit 1 to the dialyzer 3 and is purified by the dialyzer 3, and then is returned to the vein of a patient through the venous blood circuit 2 after having been removed air bubbles from the blood by the drip chamber 5. That is, the blood of a patient can be purified by the dialyzer 3 with being extracorporeally circulated from the tip of the arterial blood circuit 1 to the tip of the venous blood circuit 2.

An overflow line 6 extends from the top (air layer side) of the drip chamber 5 for discharging outside solution (priming solution such as physiological saline solution) overflowed from the drip chamber 5. An electromagnetic valve V6 functioning as a valve means is arranged on the overflow line 6 to arbitrarily open or close the overflow line 6.

A casing of the dialyzer 3 is provided with a blood inlet port 3a, a blood outlet port 3b, a dialysate inlet port 3c (inlet of the dialysate flow route), and a dialysate outlet port 3d (outlet of the dialysate flow route) and the arterial blood circuit 1 is connected to the blood inlet port 3a and the venous blood circuit 2 is connected to the blood outlet port 3b. In addition, a dialysate introducing line La and a dialysate discharging line Lb extending from a body of the dialysis apparatus are respectively connected to the dialysate inlet port 3c and the dialysate outlet port 3d.

A large number of hollow fibers (not shown) are contained in the dialyzer 3 to form blood purification membranes for purifying the blood. Thus there are formed within the dialyzer 3 a blood flow route through which the blood of a patient flows (flow route between the blood inlet port 3a and the blood outlet port 3b) and a dialysate flow route through which the dialysate flows (flow route between the dialysate inlet port 3c and the dialysate outlet port 3d). Each hollow fiber is formed with micro apertures (pores) passing through the wall of the hollow fiber to form a hollow fiber membrane. Thus impurities in blood can pass through the membranes and flow into the dialysate.

A duplex pump (not shown) is arranged within the body of the dialysis apparatus with bridging the dialysate introducing line La and the dialysate discharging line Lb. Also within the body of the dialysis apparatus there is arranged a ultrafiltration pump (not shown) for removing water from the blood of a patient flowing in the dialyzer 3. One end of the dialysate introducing line La is connected to the dialysate inlet port 3c as described above and its other end is connected to the dialysate supplying apparatus (not shown) for preparing dialysate of predetermined concentration. Also, one end of the dialysate discharging line Lb is connected to the dialysate outlet port 3d of the dialyzer 3 as described above and its other end is connected to a solution discharging means (not shown). Accordingly, the dialysate supplied from the dialysate supplying apparatus flows into the dialyzer 3 through the dialysate introducing line La and then is sent from the dialyzer 3 to the discharging means (not shown) through the dialysate discharging line Lb.

An electromagnetic valve V4 is arranged intermediate (between the duplex pump and the dialyzer 3) of the dialysate introducing line La for opening and closing the line La, and an electromagnetic valve V5 is arranged intermediate (between the duplex pump and the dialyzer 3) of the dialysate discharging line Lb for opening and closing the line Lb. In addition electromagnetic valves V1 and V2 are arranged intermediate respectively of the arterial blood circuit 1 and the venous blood circuit 2 at positions near their tips (connectors c and d) for opening and closing the circuits 1 and 2. Furthermore an electromagnetic valve V3 is arranged intermediate of the priming solution supplying line Lc for opening and closing it.

An arterial bubble detecting means 9 is arranged on the arterial blood circuit 1 at a position near its tip "c" for detecting bubbles existing in solution flowing the circuit 1 and a venous bubble detecting means 10 is arranged on the venous blood circuit 2 at a position near its tip "d" for detecting bubbles existing in solution flowing the circuit 2. In the drawings reference numerals 11 and 12 denote blood discriminators arranged at positions near the tips "c" and "d" respectively of the arterial blood circuit 1 and the venous blood circuit 2 and reference numerals 13, 14 and 15 denote tube detectors arranged respectively on the arterial blood circuit 1 and the venous blood circuit 2 at positions near the tips "c" and "d" and on the priming solution supplying line Lc.

These electromagnetic valves V1-V6 are controlled by a control means 16 such as a microcomputer for controlling opening and closing so as to open and close their related flowing lines. Especially the control means 16 of the present invention are electrically connected to these electromagnetic valves V1-V6 and the blood pump 4 and adapted to receive detecting signals from the venous bubbles detecting means 10 and to control them.

The priming solution containing means (so-called "physiological saline solution bag") 7 comprises a flexible clear container for containing a predetermined amount of the physiological saline solution (priming solution) and is suspended e.g. from a tip of a pole (not shown) projected from the body of the dialysis apparatus. The priming solution supplying line Lc is connected to the arterial blood circuit 1 at a position (connected portion P) between the arterial puncture needle "a" and the blood pump 4 to supply the physiological saline solution (priming solution) in the containing means 7 into the blood circuit. A drip chamber 8 for priming solution is connected to the priming solution supplying line Lc at intermediate thereof so that the supply (dripping) of the priming solution can be observed.

When performing the priming (operation of washing the blood flow route or the dialysate flow route with passing the priming solution therethrough and of previously charging these flow route with the priming solution) before dialysis treatment, it is possible to communicate the arterial blood circuit 1 and the venous blood circuit 2 each other by connecting the tips (concretely connectors "c" and "d") each other.

According to the dialysis apparatus (blood purification apparatus) of the present invention, the control means 16, as described above, can control the electromagnetic valves V1-V6 and the blood pump 4 by receiving detecting signals from the venous bubbles detecting means 10. Thus the control means 16 can sequentially control following steps under a condition in which the blood inlet port 3a of the dialyzer (blood purification means) 3 is set at a top position: a priming solution pool forming step for forming a priming solution pool within the drip chamber 8, an overflowing step in which the priming solution is supplied to the drip chamber 5 from the priming solution supplying line Lc via the venous blood circuit 2 by its own weight and then discharged through the over flow line 6 by stopping the blood pump 4 and opening the electromagnetic valve (valve means) V6; a circulating step in which the priming solution is supplied to the arterial blood circuit 1 from the priming solution supplying line Lc via the venous blood circuit 2 and the dialyzer (blood purification means) 3 by driving the blood pump 4 in reverse and closing the valve means V6; and a shifting step for shifting the circulating step to the overflowing step so long as the venous bubble detecting means 10 detects bubbles. In addition the control means 16 of the present invention repeatedly perform the overflow step and the circulating step until the venous bubble detecting means 10 does not detect any bubbles.

Figure 8:
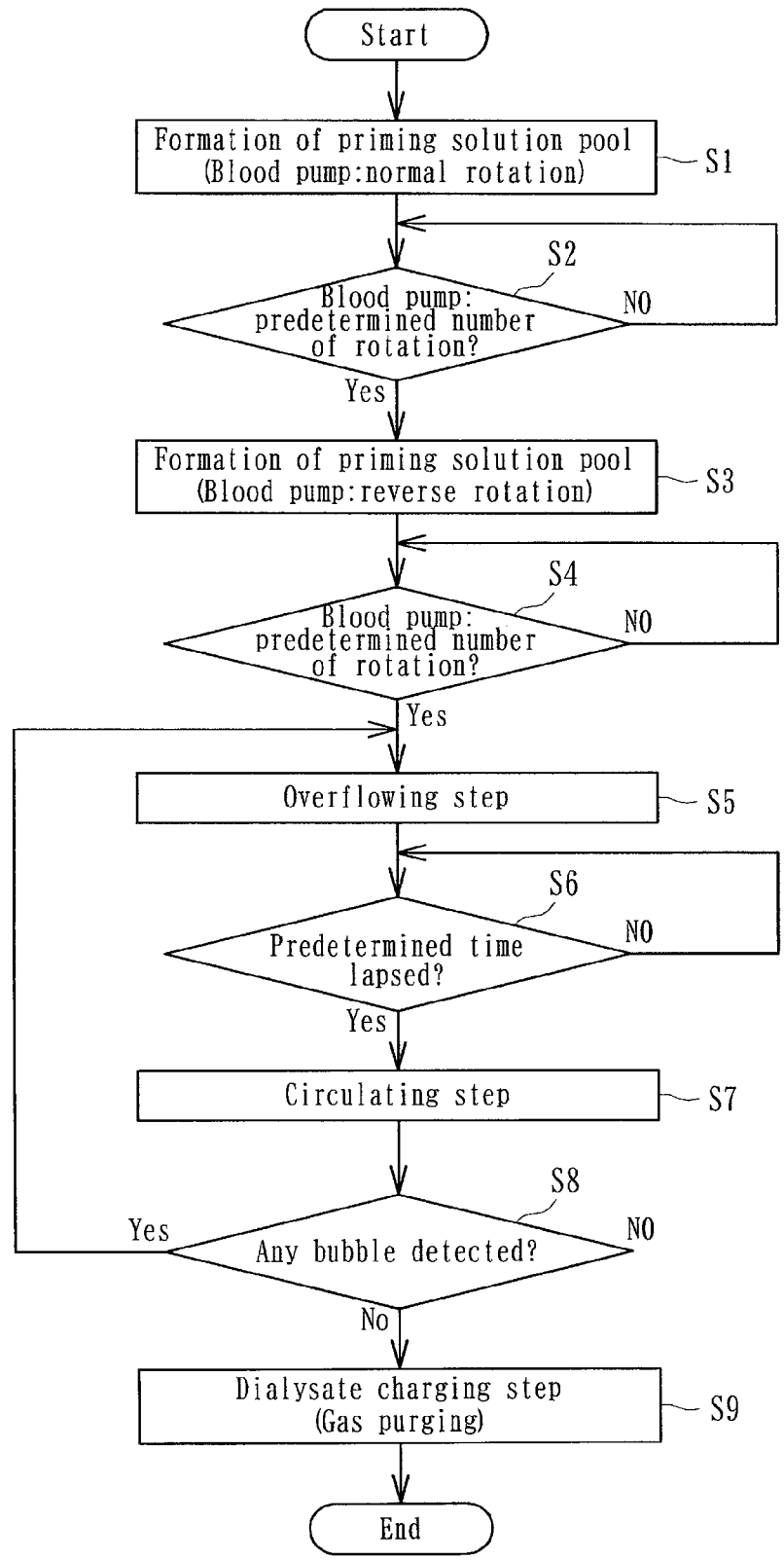
[FIG. 8] A flowchart showing controlling contents performed by a controlling means in the dialysis apparatus of FIG. 1.

The priming steps performed by the dialysis apparatus of the present invention will be hereinafter described with reference to a flowchart of FIG. 8.

Figure 2:
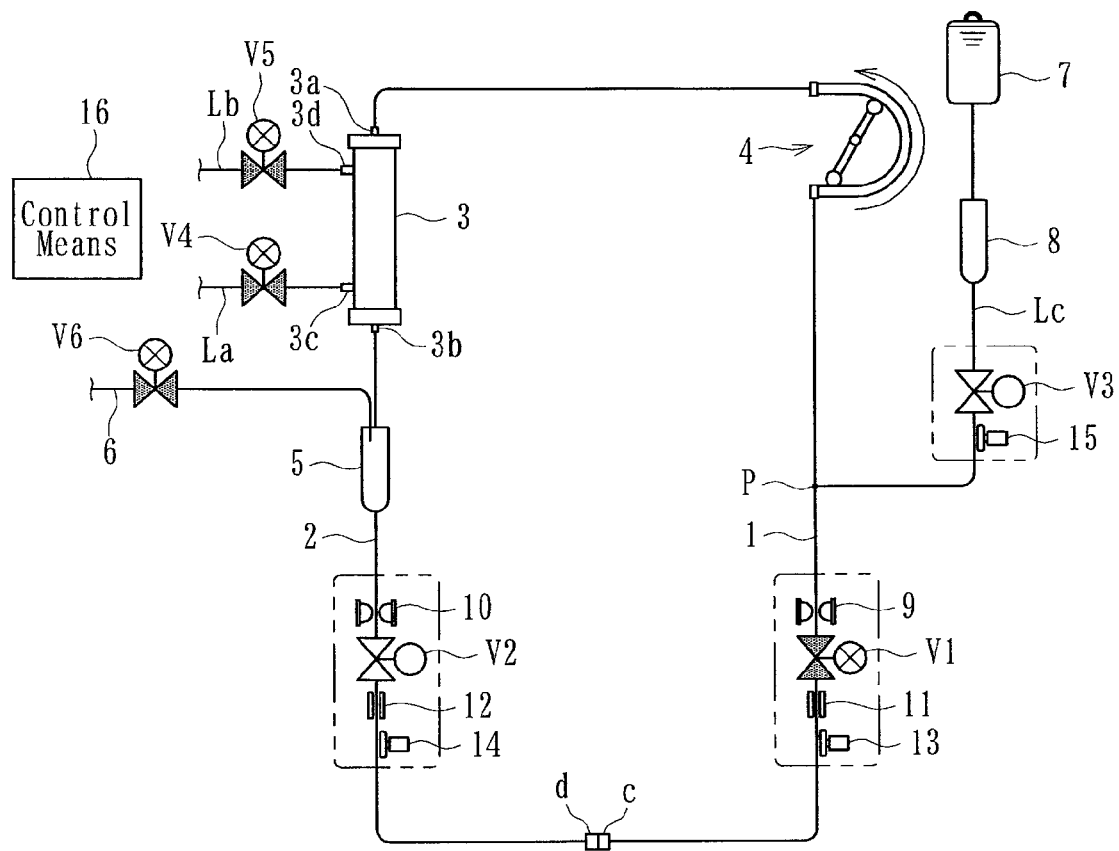
[FIG. 2] A schematic view showing a condition in which a priming solution pool forming step (under normal rotation of blood pump) performed in the dialysis apparatus of FIG. 1.

The priming solution pool forming step (S1-S4) is performed after setting the position of the blood inlet port 3a of the dialyzer 3 upward and communicating the arterial blood circuit 1 and the venous blood circuit 2 each other by connecting the connectors "c" and "d" as shown in FIG. 2. In this step, the blood pump 4 is driven in the normal direction and the physiological saline solution (priming solution) in the containing means 7 is led to the connected portion P of the artery blood circuit 1 via the priming solution supplying line Lc.

Figure 3:
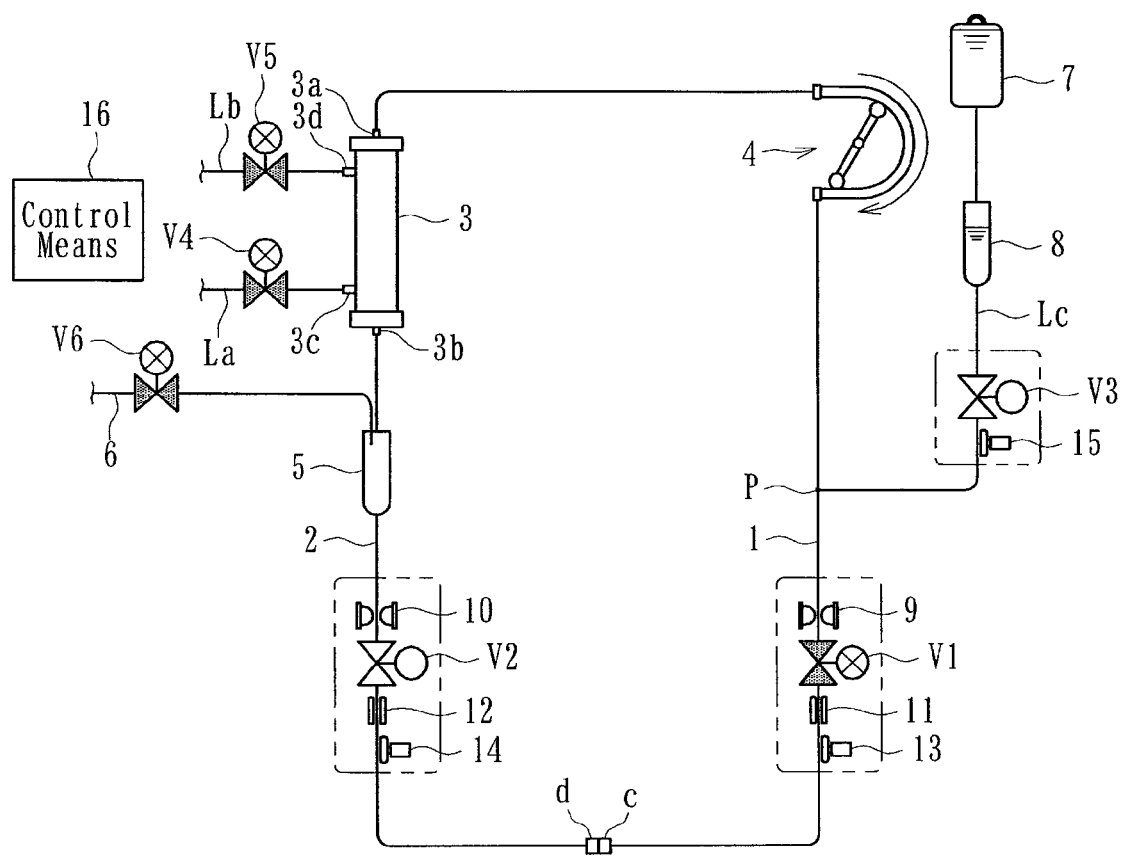
[FIG. 3] A schematic view showing a condition in which a priming solution pool forming step (under reverse rotation of blood pump) performed in the dialysis apparatus of FIG. 1.

Then it is decided whether the blood pump 4 has been rotated a predetermined number of rotation (e.g. 5 rotations) in the normal direction or not (S2) and the blood pump 4 is rotated in the reverse direction when the predetermined number of rotation has been rotated (S3, see FIG. 3). Then it is decided whether the blood pump 4 has been rotated a predetermined number of rotation (e.g. 2 rotations) in the reverse direction or not (S4) and the blood pump 4 is stopped when the predetermined number of rotation has been rotated and a series of the priming solution pool forming steps are completed. Thus the pool of the physiological saline solution is formed in the drip chamber 8 for priming solution. When the blood pump 4 is rotated in the normal direction (S1) and in the reverse direction (S3), the electromagnetic valves V2 and V3 are opened and the electromagnetic valves V1 and V4-V6 are closed.

Figure 4:
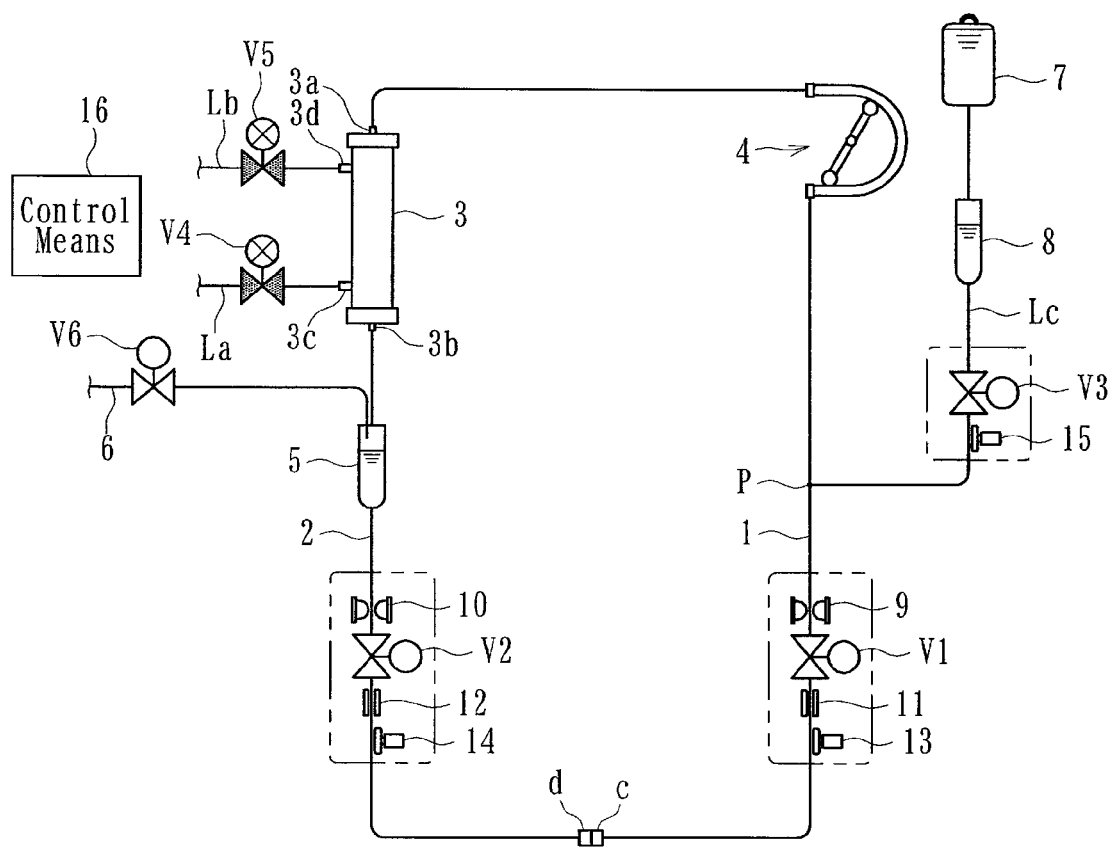
[FIG. 4] A schematic view showing a condition in which an initial overflowing step is performed in the dialysis apparatus of FIG. 1.

Then as shown in FIG. 4 the physiological saline solution (priming solution) is supplied by its own weight to the drip chamber 5 from the priming solution supplying line Lc via the venous blood circuit 2 and discharged from the drip chamber 5 through the overflow line 6 by stopping the blood pump 4 and opening electromagnetic valves V6 and V1 (overflowing step S5). That is, the physiological saline solution (priming solution) in the containing means 7 is fed by its own weight (head pressure) to the drip chamber 5 through the priming solution supplying line Lc, the connected portion P and the connector "c" on the arterial blood circuit 1 and the connector "d" on the venous blood line 2 and discharged through the overflow line 6 extending from the top of the drip chamber 5.

Figure 5:
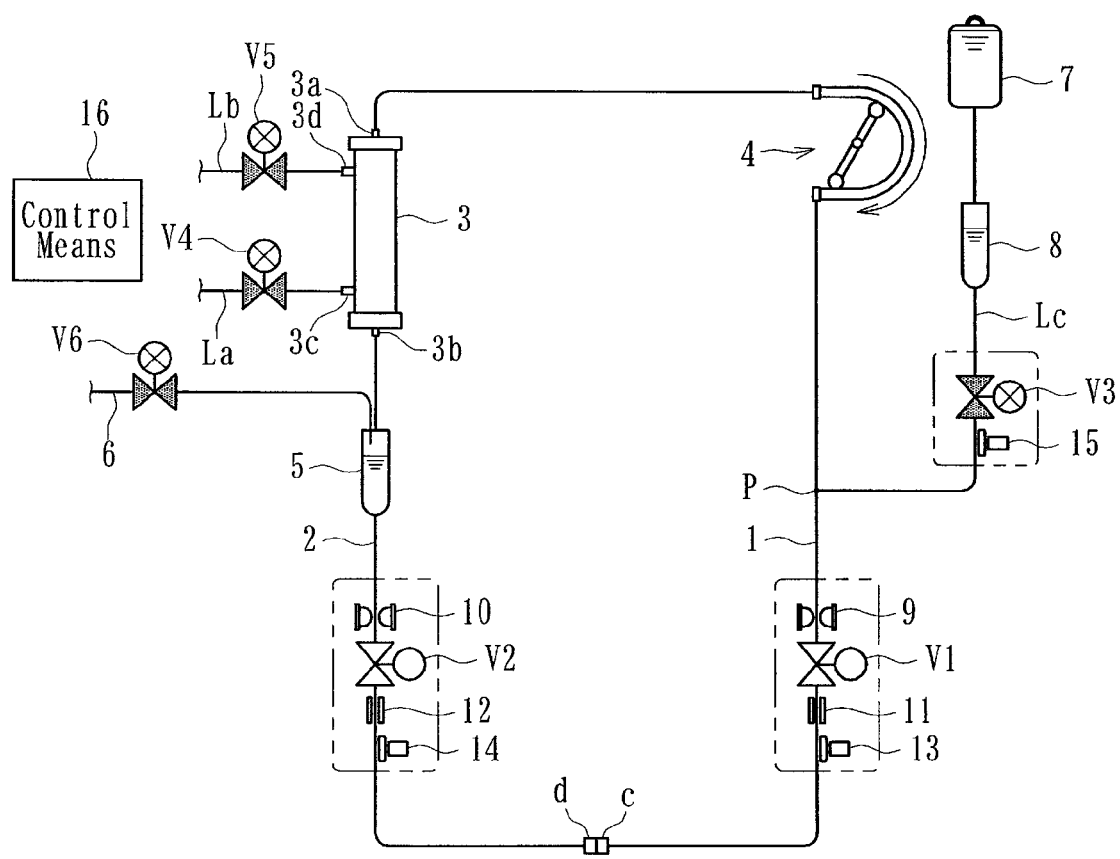
[FIG. 5] A schematic view showing a condition in which a circulating step is performed in the dialysis apparatus of FIG. 1.

Then it is decided whether a predetermined time (e.g. 30 seconds) has been lapsed from the commencement of the overflowing step S5 or not (S6) and then the circulating step is performed when the predetermined time has been lapsed (S7). As shown in FIG. 5, the circulating step is a step in which the physiological saline solution (priming solution) is supplied to the arterial blood circuit 1 from the priming solution supplying line Lc via the venous blood circuit 2 and the dialyzer 3 with driving the blood pump 4 in the reverse direction (preferably at a driving speed of e.g. 100 mL/min) and closing electromagnetic valves V6 and V3. Thus the physiological saline solution can flow through the blood flow route within the dialyzer 3 from its bottom to top and accordingly the bubbles can smoothly move upward to be purged.

Figure 6:
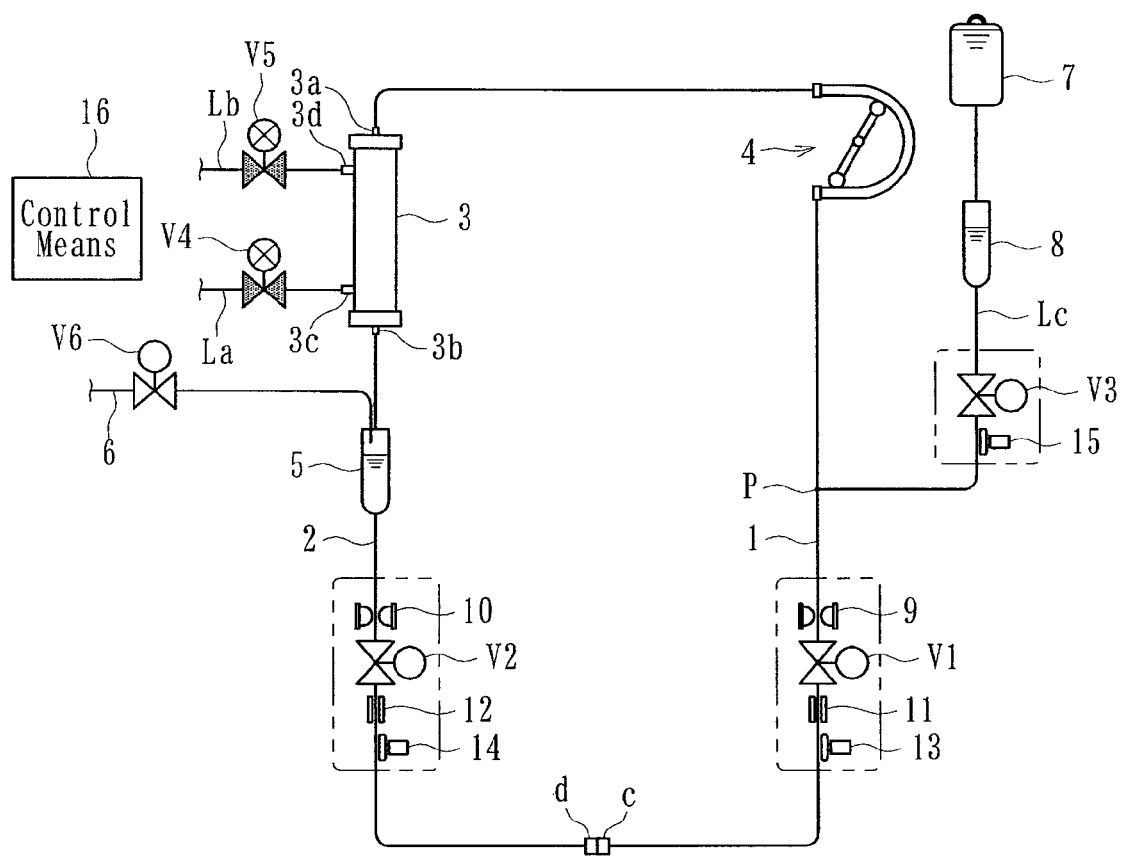
[FIG. 6] A schematic view showing a condition in which a overflowing step is performed in the dialysis apparatus of FIG. 1.

It is decided whether the venous bubble detecting means 10 has detected or not after the circulating step S7 (S8) and then is returned to the step S5 when bubbles are detected and again shifted to the overflowing step S5. As shown in FIG. 6, in this overflowing step S5, although the physiological saline solution is contained in the drip chamber 5, other operations are similar to those in FIG. 4 and thus the blood pump 4 is stopped and the electromagnetic valves V3 and V6 are opened. During which although the duplex pump (not shown) bridged between the dialysate introducing line La and the dialysate discharging line Lb is operated, the dialysate cannot be supplied to the dialyzer 3 since the dialysate is bypassed through a bypass line (not shown). Then after the overflowing step S5 and the circulating step S7 having been performed again, it is decided again in the step S8 whether bubbles are detected or not. Accordingly the overflowing step S5 and the circulating step S7 are repeatedly continued until any bubble cannot be detected by the venous bubble detecting means 10.

Figure 7:
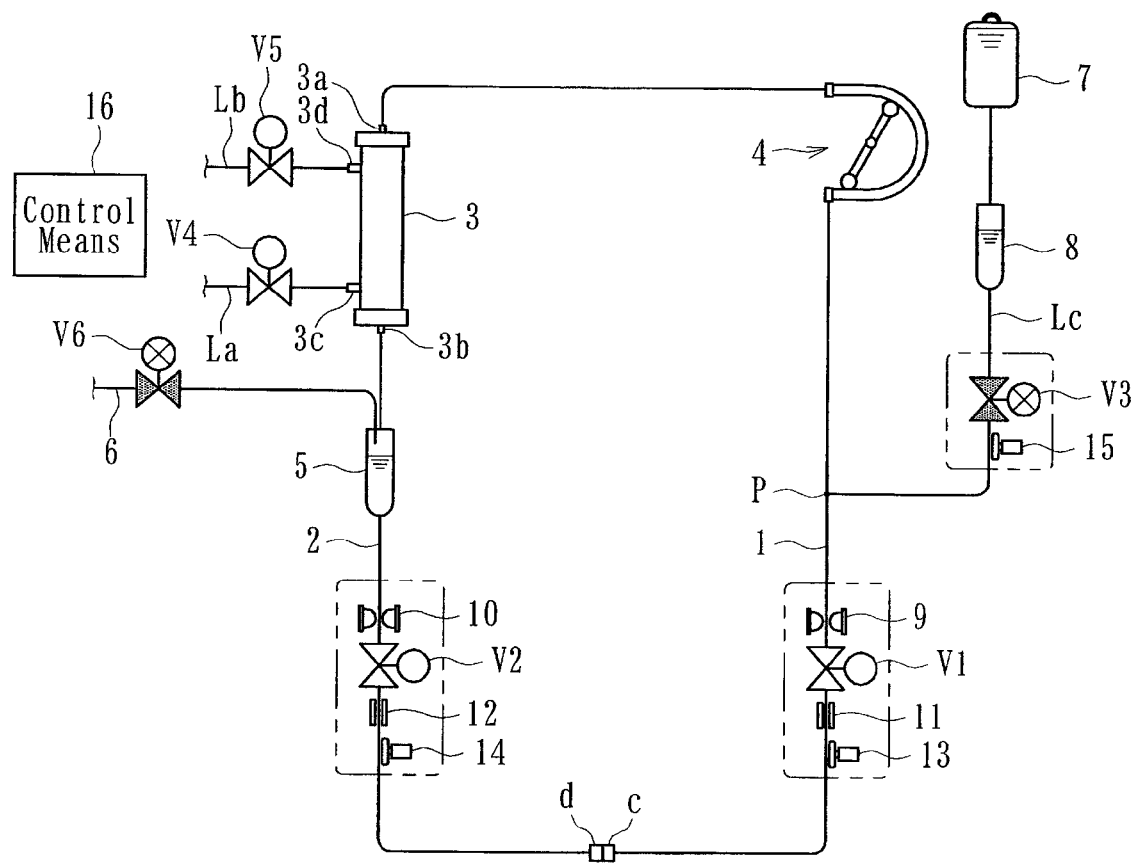
[FIG. 7] A schematic view showing a condition in which a dialysate charging step is performed in the dialysis apparatus of FIG. 1.

When any bubble cannot be detected by venous bubble detecting means 10 it is proceeded to a step S9 and the dialysate charging step (so-call gas purging step) is performed. This dialysate charging step S9 is a step in which the duplex pump is driven with opening the valves V4 and V5 to charge the dialysate flow route within the dialyzer 3 with dialysate solution as shown in FIG. 7. In this time the electromagnetic valves V3 and V6 are closed and V1, V2, V4 and V5 are opened.

It is preferable to discharge the priming solution by overflowing it from the drip chamber 5 with driving the blood pump 4 in the normal direction and opening the electromagnetic valves V3 and V6 before shifting to the dialysate charging (gas purging) step or during or after gas purging. In this case it is possible to perform additional washing the inside of the dialyzer 3. The blood pump 4 may be driven during the dialysate charging (gas purging) step. In addition it is also possible to wash the follow fiber membranes (i.e. pores of the hollow fibers) within the dialyzer 3 by feeding the priming solution from the blood side of the blood flow route (hollow fibers) to the dialysate side with opening the electromagnetic valve V3, driving the blood pump 4 and additionally driving the ultrafiltration pump on the dialysate flowing pipes.

According to the present invention it is possible to carry out the washing or priming of portions through which blood or dialysate can flow during the dialysis treatment and thus to positively purge bubbles therefrom by performing the priming solution pool forming step, the overflowing step, the circulating step and the dialysate charging step. Furthermore according to the present invention, since all the priming steps are performed under the condition in which the blood inlet port 3a of the dialyzer 3 is directed upward, it is possible to easily automate all the priming steps and to quickly and positively perform the air purging of the dialyzer 3.

In addition according to the present invention, since it is shifted to the overflowing step by bubble detection by the venous bubble detection means 10 in the circulating step, it is possible to easily automate the priming operation and positively and smoothly perform the air bubble purging of the dialyzer (blood purification means) 3. Especially since the physiological saline solution (priming solution) is never fed to the blood flow route in the dialyzer 3 from the top to the bottom thereof in priming operation, it is possible to surely prevent the air lock which would be caused thereafter.

Further according to the present invention, since the overflowing step and the circulating step are repeatedly performed until any air bubble cannot be detected by the venous bubble detecting means 10, it is possible to more positively discharge bubbles in the blood flow route during priming operation. In addition since the priming solution pool forming step is performed for forming the priming solution pool in the drip chamber 8 before the initial overflowing step, it is possible to form the priming solution pool in the drip chamber 8 during the priming operation.

In addition according to the present invention, since the priming operation can be performed under a series of controls by the control means 16, it is possible to easily automate the priming operation and thus to remarkably reduce manual operations to be performed by medical personnel. Furthermore it is possible to achieve the blood purification apparatus (dialysis apparatus) of the present invention by applying the control contents of the control means 16 to an existing blood circuit of the blood purification apparatus.

In addition it is possible to construct the control means 16 so that it performs, during the priming operation, the dialysate charging step before the initial overflowing step S5 by connecting the dialysate introducing line La and dialysate discharging line Lb respectively to the dialysate inlet port 3c and the dialysate outlet port 3b of the dialyzer (blood purification means) 3. Such a structure enables to prevent generation of bubbles in the priming solution since that air in the dialysate flow route moves to the blood flow route via blood purification membranes during steps from the overflowing step S5 to the circulating steps S7 performed thereafter. In addition since the dialysate introducing line La and dialysate discharging line Lb are connected to the dialyzer 3 via e.g. couplers on commencement of priming, it is possible to prevent entering of foreign matters such as dusts into the dialyzer 3 during priming operation and thus to further improve the safety in priming.

If the blood purification apparatus is modified so that dialysate charging step for charging the dialysate flow route in the dialyzer 3 with dialysate is performed by connecting the dialysate introducing line La and dialysate discharging line Lb respectively to the dialysate inlet port 3c and the dialysate outlet port 3b of the dialyzer 3 before the initial overflowing step S5 during the priming operation as described above, the apparatus may be advantageously applied to a so-called plate type blood purification means.

Figure 11:
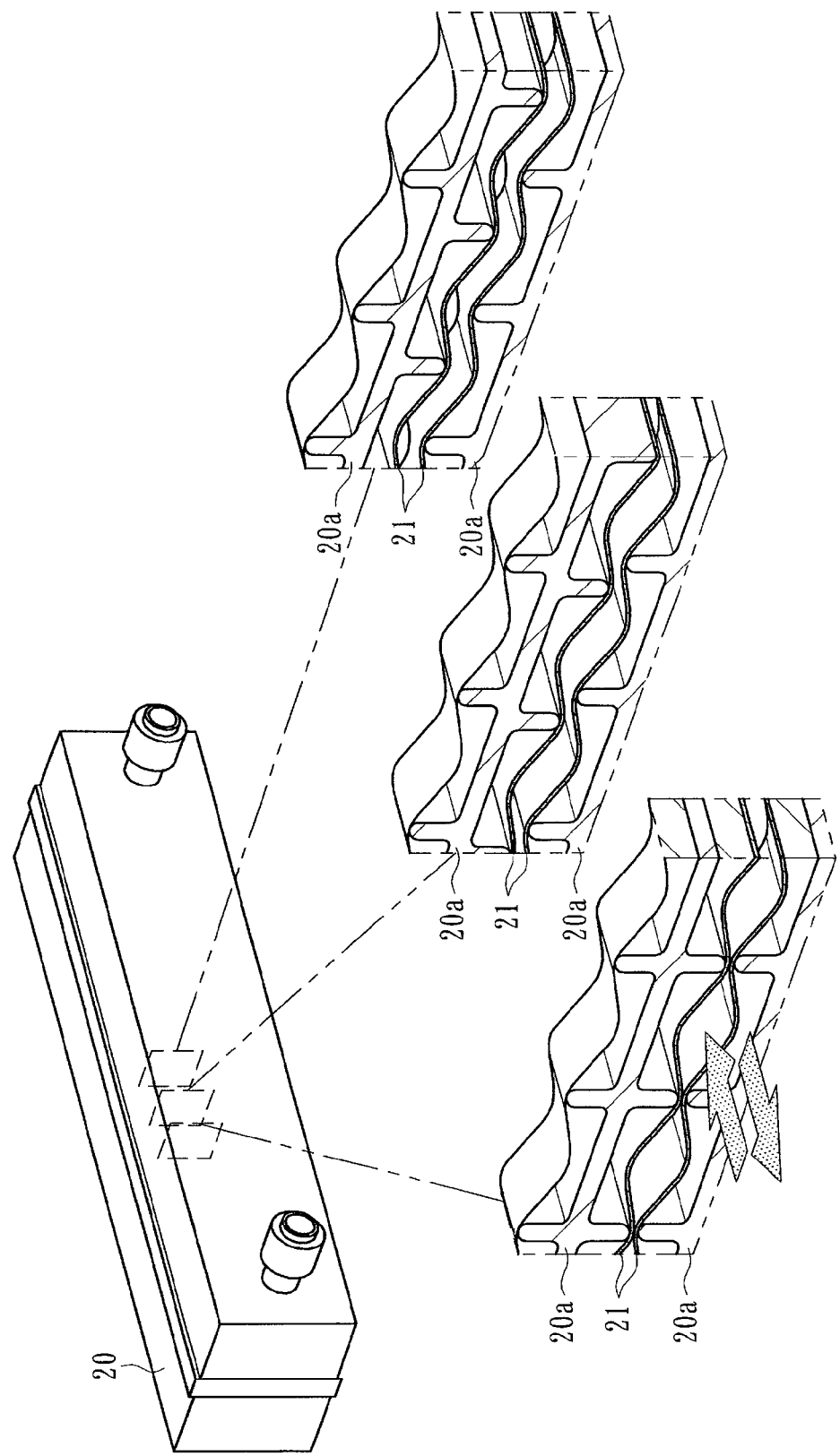
[FIG. 11] A schematic view showing a so-called plate type blood purification means (dialyzer) applied to the dialysis apparatus (blood purification apparatus) of the present invention.
Figure 12:
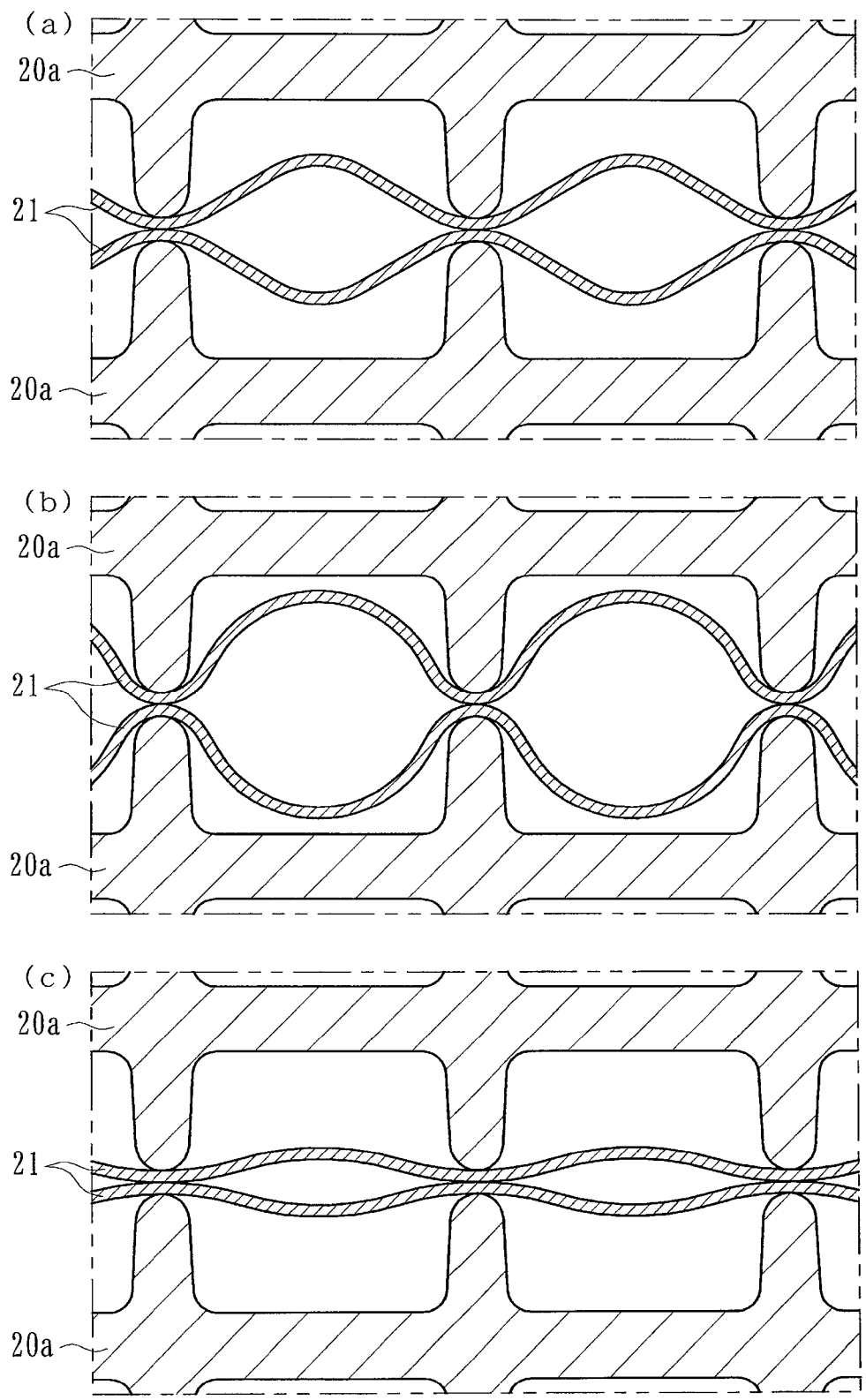
[FIG. 12] A schematic view showing several conditions of filtrating membranes used in the plate type blood purification means (dialyzer) in which (a) is a condition of priming solution flowing under a normal pressure, (b) is a condition of priming solution flowing under a high pressure, and (c) is a condition of priming solution flowing under a low pressure.

Such a so-called plate type blood purification means has a structure as shown in FIG. 11 which has a casing 20 in which a plurality of secured plates 20a are arranged. Filtration membranes 21 of sheet configuration are sandwiched between the secured plates 20a to form blood flow routes therebetween and dialysate flow routes between the filtrating membranes 21 and the secured plates 20a. Thus the plate type blood purification means (dialyzer) comprises plurality of filtrating membranes 21 of blood purification membranes and is formed so that it has different flowing volumes between the filtrating membranes 21 in a case in which solution (priming solution or blood) flows in the blood flow route at a normal fluid pressure (see FIG. 12(a)), a case in which solution flows at a high fluid pressure (see FIG. 12(b)), and a case in which solution flows at a low fluid pressure (see FIG. 12(c)). According to such a plate type blood purification means (dialyzer), since the blood flow route can expand and contract in response to the fluid pressure, it is possible to weak a tendency of the blood pressure reduction.

As described above if the dialysate charging step for charging the dialysate flow route in the dialyzer 3 with dialysate is performed by connecting the dialysate introducing line La and dialysate discharging line Lb respectively to the dialysate inlet port 3c and the dialysate outlet port 3b of the dialyzer 3 before the initial overflowing step S5 during the priming operation, it is possible to prevent the charging solution in the dialysate flow route from being mingled with the priming solution due to flow of the charging solution into the blood flow route via the blood purification membranes during performing of the overflowing step S5 through the circulating step S7 when the apparatus is applied to a so-called wet type blood purification means in which the charging solution is previously charged in the dialyzer (blood purification means) 3.

Furthermore it is preferable that the control means 16 controls during the circulating step S7 the pressure in the dialysate flow route of the dialyzer (blood purification means) 3 so that it becomes a negative pressure. According to the blood purification apparatus of the present invention since it has the ultrafiltration pump for removing water from the blood of a patient flowing through the dialyzer 3 as described above, it is possible to reduce the pressure in the dialysate flow route of the dialyzer 3 to the negative pressure by driving the ultrafiltration pump. The ultrafiltration pump is a pump usually formed on a line bypassed the duplex pump (driving means for supplying the dialysate) on the dialysate discharging line Lb.

If the pressure in the dialysate flow route of the dialyzer (blood purification means) 3 is reduced to the negative pressure during the circulating step S7, it is possible to positively assure the flowing volume of the blood flow route and thus to attain a more smooth passage of the priming solution through the blood flow route. Especially when it is applied to the so-called plate type blood purification means (see FIGS. 11 and 12), it is possible to positively assure the flowing volume of the blood flow route with expanding the blood flow route between the filtration membranes 21 of sheet configuration.

As described above, if the pressure in the dialysate flow route of the dialyzer (blood purification means) 3 is reduced to the negative pressure, it is possible to eliminate any separate means for reducing the pressure in the dialysate flow route. If it is means for reducing the pressure in the dialysate flow route of the dialyzer 3 to the negative pressure during the circulating step S7, other means (e.g. means for such as a driving source or separate and new means arranged in the blood purification apparatus) may be used. In addition it is sufficient if the pressure in the dialysate flow route in the dialyzer 3 is lower than that in the blood flow route and it is not always necessary to make the pressure negative as in this embodiment.

Furthermore it is possible to form the dialysis apparatus so that the blood pump 4 is driven in the normal direction by a predetermined time duration or a predetermined number of rotation after the overflowing step S5 and before the circulating step S7 (i.e. a time duration between the overflowing step S5 and the circulating step S7). More concretely for example the charging solution (distilled water) previously charged in the blood flow route within the dialyzer 3 or the priming solution supplied from the containing means 7 flows into the drip chamber 5 and fill this line (flow route from the blood outlet port 3b of the dialyzer 3 on the venous blood circuit 2 to the drip chamber 5) by driving the blood pump 4 relatively slowly in the normal direction at a point of time of completion of the overflowing step S5. During the normal rotation driving of the blood pump 4, it is preferable to open the electromagnetic valve V3 and close the electromagnetic valve V6.

Thus it is possible by driving the pump 4 in the normal direction, to remove bubbles in the flow route from the blood outlet port 3b of the dialyzer 3 on the venous blood circuit 2 to the drip chamber 5 before the circulating step S7 and accordingly to perform the priming operation more smoothly and in a short time. Especially when using the dialyzer (blood purification means) of the so-called dry type which is not filled with the charging solution, if air is once entered into the dialyzer a great deal of priming solution is required to remove the air and thus the priming solution is wasted and a longer time is required. On the contrary when driving the blood pump 4 in the normal direction, these problems can be solved and thus an efficient priming operation can be performed.

Figure 9:
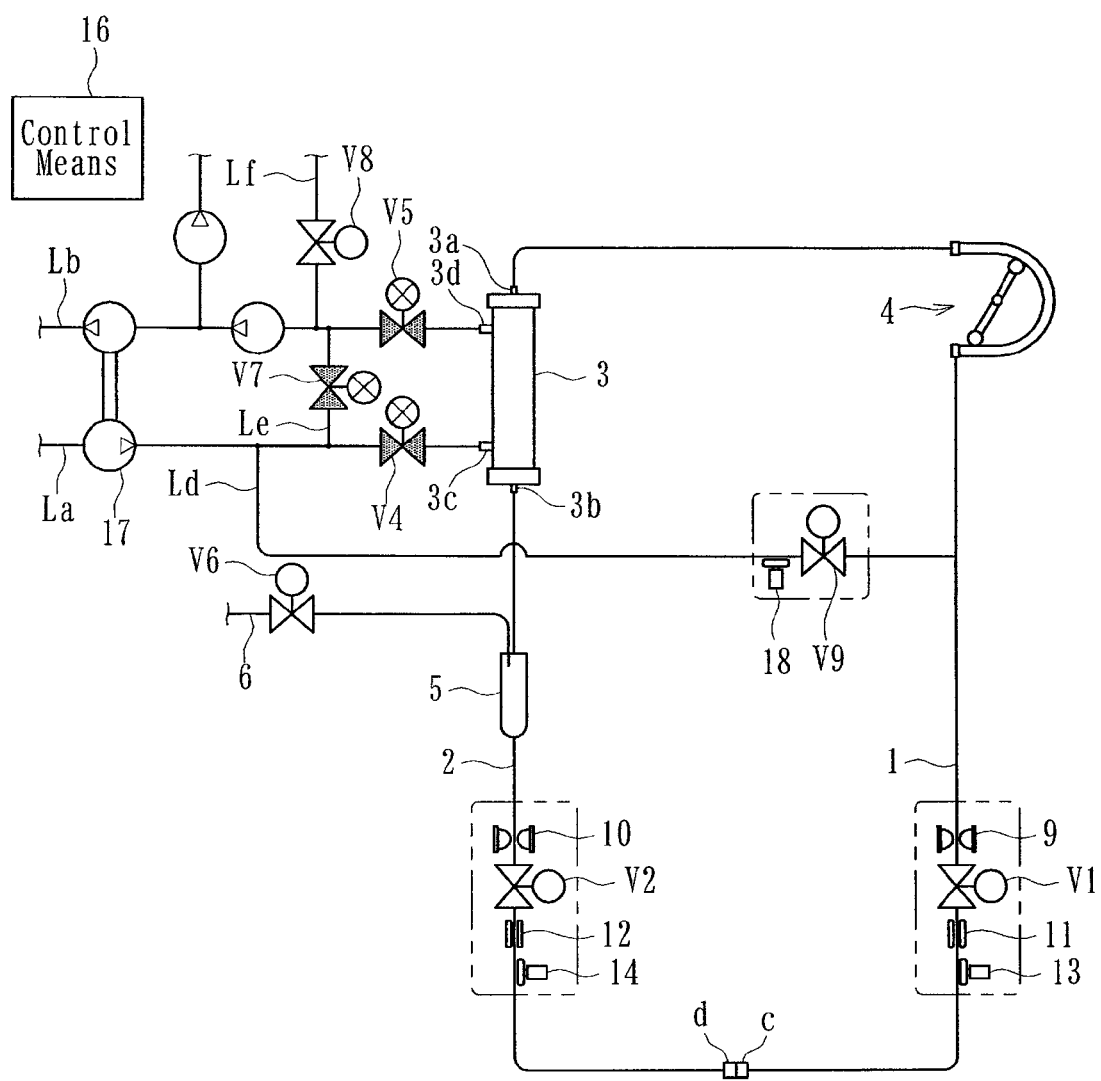
[FIG. 9] A schematic view showing a condition in which a overflowing step is performed in a dialysis apparatus (blood purification apparatus) of another embodiment.

The present invention is not limited to the embodiments described above and the priming solution may be supplied without relying on its own weight in the overflowing step. For example as shown in FIG. 9, it is possible to connect the priming solution supplying line Ld to a position between the downstream of the duplex pump 17 on the dialysate introducing line La and the upstream of the blood pump 4 on the arterial blood circuit 1. In FIG. 9 reference numerals 18 and V9 denote a tube detector and an electromagnetic valve on the priming solution supplying line Ld respectively, reference characters Le and V7 denote a bypass line connecting the dialysate introducing line La and the dialysate discharging line Lb, and an electromagnetic valve on the bypassline respectively, and reference characters Lf and V8 denote a dialysate supplying line for supplying the dialysate solution to the dialysate discharging line Lb, and an electromagnetic valve on the dialysate supplying line respectively.

According to the embodiment of FIG. 9, it is possible to supply the dialysate (priming solution) from the priming solution supplying line Ld to the drip chamber 5 via the venous blood circuit 2 and to discharge it from the overflow line 6. In the overflowing step the dialysate is introduced to the side of the dialysate discharging line Lb of the duplex pump 17 via the supplying line Lf with the electromagnetic valves V4, V5 and V7 being closed and V6 and V8 being opened as shown in FIG. 9.

Thus according to the embodiment of FIG. 9, since no head is required as compared with the previous embodiment in which the priming solution is supplied using its own weight, arrangement or mounting of the priming solution supplying line Ld is not limited. In addition since the supplying amount of the dialysate as the priming solution can be controlled by controlling the discharging amount of the duplex pump 17, it is possible to more exactly and surely perform the overflowing step. Furthermore since the price of the dialysate is lower in general than that of the physiological saline solution, it is possible to suppress the cost of operation of the dialysis apparatus.

Figure 10:
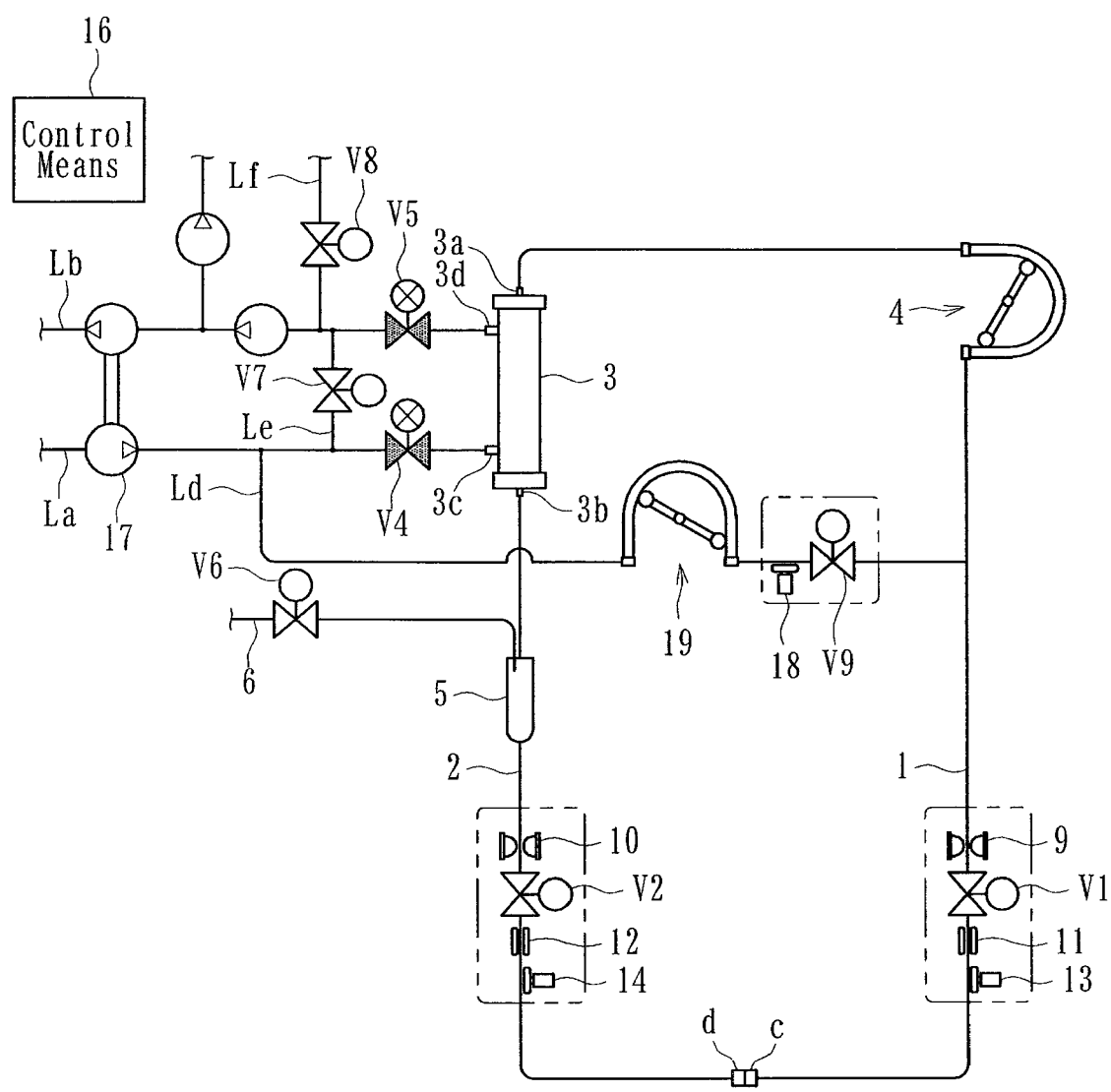
[FIG. 10] A schematic view showing a condition in which a overflowing step is performed in a dialysis apparatus (blood purification apparatus) of a further embodiment.

As shown in FIG. 10, it is possible as a further embodiment to construct the dialysis apparatus so that a dialysate pump 19 (peristaltic pump same as the blood pump 4) is arranged on the priming solution supplying line Ld and the dialysate is supplied during the overflowing step by driving the dialysate pump 19. Also in this embodiment since no head is required as compared with the previous embodiment in which the priming solution is supplied using its own weight, arrangement or mounting of the priming solution supplying line Ld is not limited. In addition since the supplying amount of the dialysate as the priming solution can be controlled by controlling the discharging amount of the dialysate pump 19, it is possible to more exactly and surely perform the overflowing step. Furthermore since the price of the dialysate is lower in general than that of the physiological saline solution, it is possible to suppress the cost of operation of the dialysis apparatus.

Figure 13:
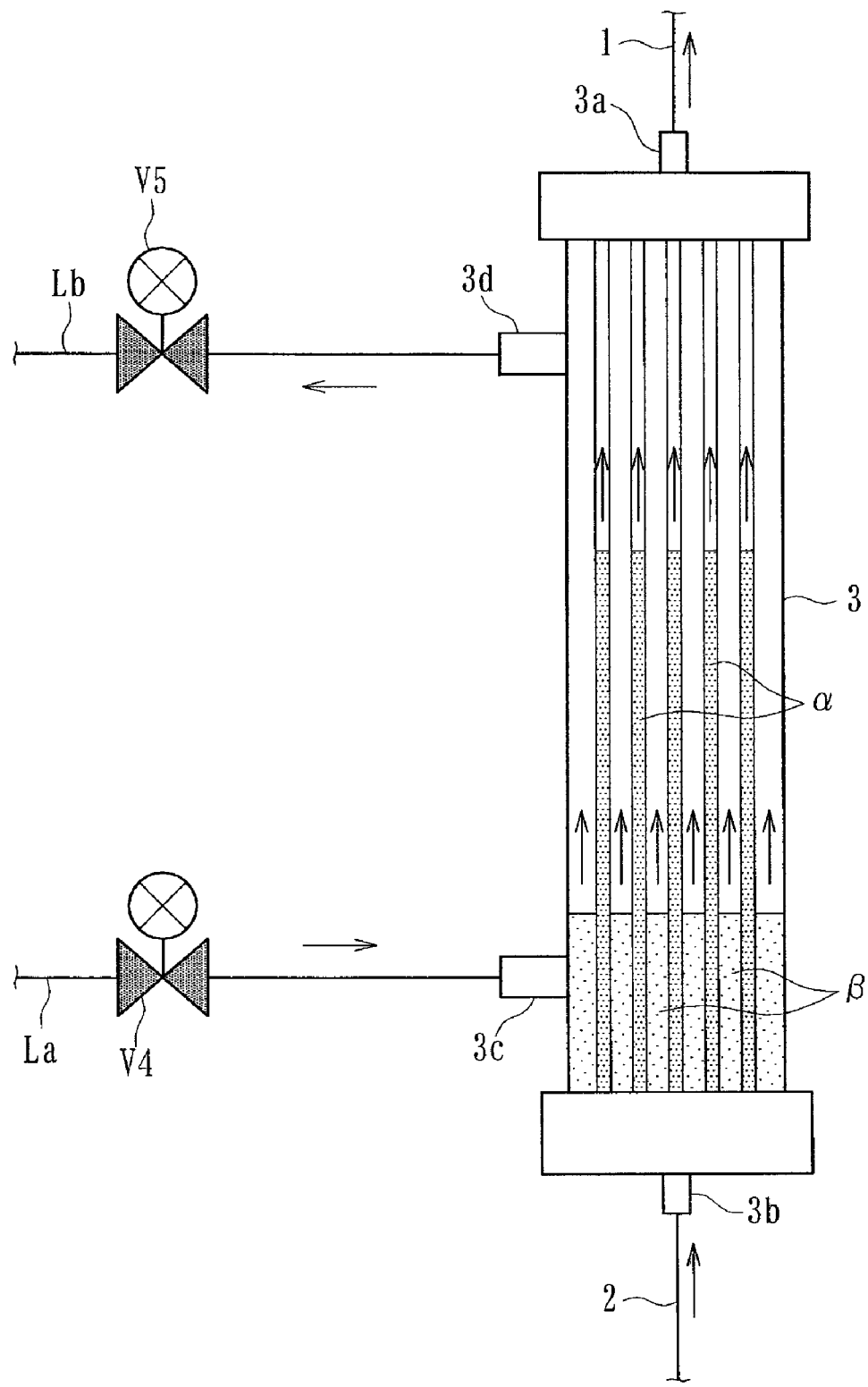
[FIG. 13] A schematic view showing a condition of an inside (blood flow route and dialysate flow route) of a blood purification means (dialyzer) during the circulating step in a yet further embodiment of the present invention.
Figure 14:
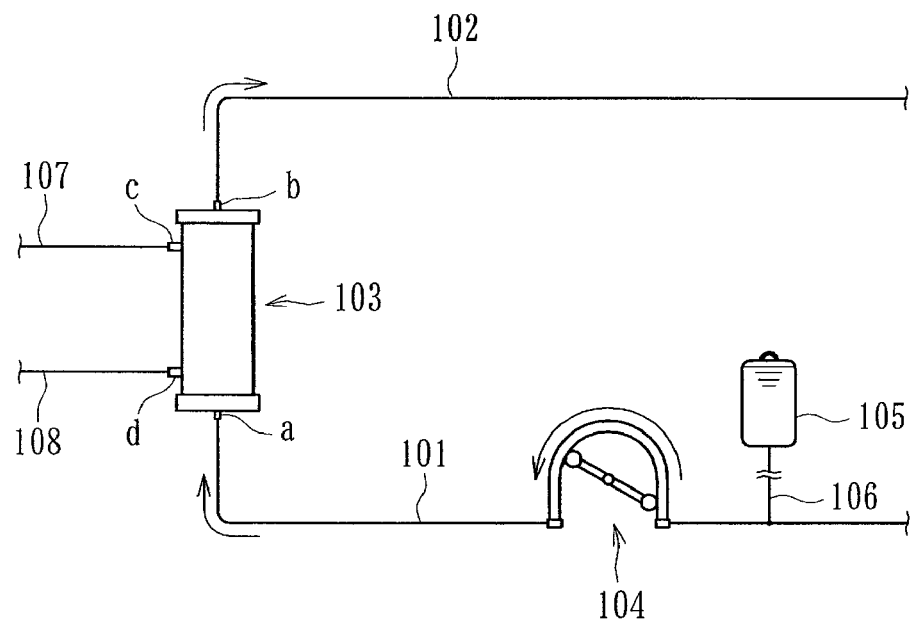
[FIG. 14] A schematic view showing a condition in which a priming step (blood flow route) performed in a dialysis apparatus of the prior art.
Figure 15:
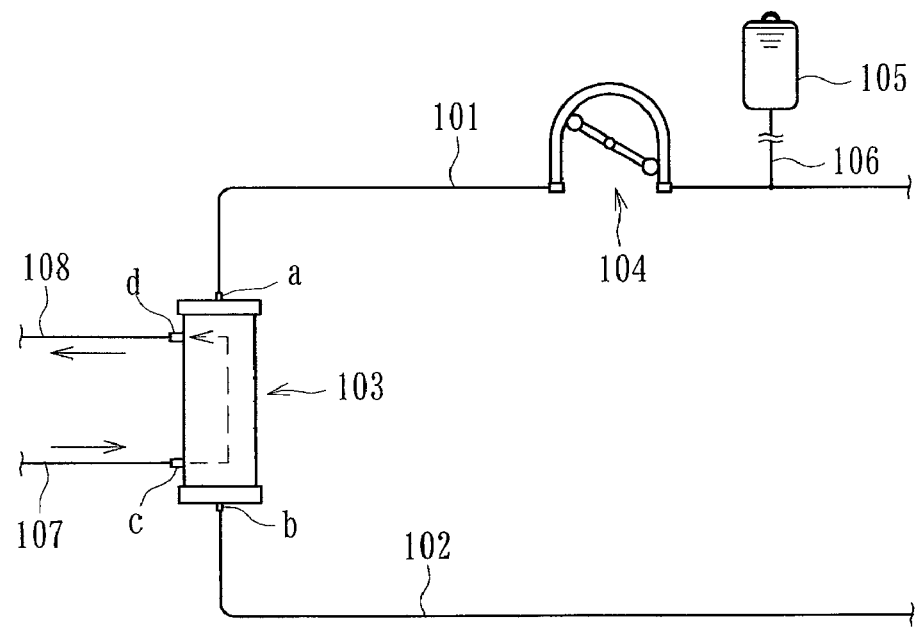
[FIG. 15] A schematic view showing a condition in which a priming step (dialysate flow route) performed in a dialysis apparatus of the prior art.

According to a yet further embodiment shown in FIG. 13, it is formed in the circulating step (S7) that the dialysate flow route sideβ can be charged with the dialysate by driving the duplex pump (not shown in FIG. 13) with the electromagnetic valves V4 and V5 being opened at a point of time in which a predetermined amount of the physiological saline solution (priming solution) is sent to the blood flow routeα by the blood pump 4 (the priming solution is sent to the blood flow routeα at an amount of about one half volume of the blood flow routeα). For charging the dialysate flow routeβ with the dialysate, it is performed so that the dialysate does not exceed the solution level in the blood flow routeα (i.e. so that the solution level in the dialysate flow routeβ is always remained lower than that in the blood flow routeα) (This is performed for example by driving the duplex pump at a speed lower than that of the blood pump 4 or by operating the duplex pump by about one shot (16.7 mL) relative to the discharging amount of the blood pump 4 (about 20 mL)).

That is, for performing the circulating step (S7) as to a dialyzer that is recently developed and excellent in the solute removing ability and in permeability, it is afraid that the physiological saline solution (priming solution) would leak out from the blood flow routeα (inside of the hollow fiber membranes) to the dialysate flow routeβ (outside of the hollow fiber membranes) or that air in the dialysate flow routeβ (outside of the hollow fiber membranes) would enter into the blood flow routeα (inside of the hollow fiber membranes).

Accordingly it is afraid that the amount of the physiological saline solution (priming solution) to be used would be increased or that the priming operation itself would be impossible.

Especially in the circulating step (S7), since the pressure in the blood flow routeα is somewhat negative due to the reverse rotation of the blood pump 4, it is afraid that air in the dialysate flow routeβ (outside of the hollow fiber membranes) would enter into the blood flow routeα (inside of the hollow fiber membranes). In such a case since the physiological saline solution (priming solution) naturally to be sent out in the circulating step (S7) is not sent out and air in the dialysate flow routeβ is sent out, it is afraid that the number of the overflowing step (S5) would be increased and a large amount of the physiological saline solution (priming solution) more than an actual charging amount would be required.

When adopting the circulating step (S7) described above, it is possible to more positively prevent the air in the dialysate flow routeβ would enter into the blood flow routeα even if a dialyzer excellent in the solute removing ability and in permeability is used and thus possible to perform the priming at a usage amount of the priming solution substantially same as that used in the usual dialyzer. In addition since the dialysate flow routeβ can be charged with the dialysate while the blood flow routeα is charged with priming solution (physiological saline solution), it is possible to eliminate or prematurely complete the dialysate charging step S9 thereafter and thus to shorten the priming time.

Similarly to the previous embodiments it is also decided in this embodiment of FIG. 13 whether the venous bubble detecting means 10 has detected bubbles or not (S8) after the charging step (S7) and it returns to the step S5 and shifts again to the overflowing step S5 when the detecting means has detected the bubbles. Thus the overflowing step S5 and the circulating step S7 are repeatedly performed until the venous bubble detecting means 10 does not detect any bubble.

According to the present invention although the priming solution pool forming steps (S1-S4) are performed automatically, it is possible to eliminate the priming solution pool forming steps (S1-S4) or to manually perform them. In addition although the physiological saline solution as priming solution is supplied from the containing means 7, it is possible to supply other priming solution different from the physiological saline solution. Furthermore although it has been described that the present invention is applied to the dialysis apparatus used for dialysis treatment, it may be possible to other apparatus (e.g. a blood filtrating dialysis method, a blood filtrating method, a blood purification apparatus used in AFBF, a plasma adsorption apparatus, etc.) which can purify the blood of a patient by the extracorporeally circulation.

APPLICABILITY IN INDUSTRIES

The present invention can be applied to any other applications if they are a blood purification apparatus and its priming method in which during the priming operation the control means can sequentially control following steps under a condition in which the blood inlet port of the blood purification means is set at a top position: an overflowing step in which the priming solution is supplied to the drip chamber from the priming solution supplying line via the venous blood circuit and then discharged through the over flow line by stopping the blood pump and opening the valve means; a circulating step in which the priming solution is supplied to the arterial blood circuit from the priming solution supplying line via the venous blood circuit and the blood purification means by driving the blood pump in reverse and closing the valve means; and a shifting step for shifting the circulating step to the overflowing step so long as the venous bubble detecting means detects bubbles.

EXPLANATION OF REFERENCE NUMERALS

1 ... arterial blood circuit
2 ... venous blood circuit
3 ... dialyzer (blood purification means)
4 ... blood pump
5 ... drip chamber
6 ... overflow line
7 ... priming solution containing means
8 ... drip chamber for priming solution
9 ... arterial bubble detecting means
10 ... venous bubble detecting means
11, 12 ... blood discriminator
13, 14, 15 ... tube detector
16 ... control means
La ... dialysate introducing line
Lb ... dialysate discharging line
Lc ... priming solution supplying line
V1-V5 ... electromagnetic valve
V6 ... electromagnetic valve (valve means)
α ... a blood flow route
β ... dialysate flow route

What is claimed is:

1. A blood purification apparatus comprising:
   a blood circuit including an arterial blood circuit and a venous blood circuit for extracorporeally circulating the blood of a patient from a tip of the arterial blood circuit to a tip of the venous blood circuit;
   a dialyzer for purifying the blood of a patient flowing through the blood circuit interposed between the arterial blood circuit and the venous blood circuit of the blood circuit and formed with a blood flow route through which the blood of a patient flows and a dialysate flow route through which dialysate flows via blood purification membranes arranged therebetween;
   a blood pump arranged in the arterial blood circuit;
   a dialysate introducing line and a dialysate discharging line connected respectively to an inlet port and an outlet port of the dialysate flow route of the blood purification means;
   a priming solution supplying line connected to the arterial blood circuit for supplying priming solution to the blood circuit;
   a blood inlet port and a blood outlet port arranged at opposite ends of the dialyzer, the blood inlet port being connected to the arterial blood circuit for introducing the blood therefrom into the blood flow route within the blood purification means and the blood outlet port being connected to the venous blood circuit for discharging the blood from the blood flow route within the dialyzer;
   a dialysate inlet port and a dialysate outlet port arranged at the side of the dialyzer, the dialysate inlet port being connected to the dialysate introducing line for introducing the dialysate therefrom into the dialysate flow route within the dialyzer and the dialysate outlet port being connected to the dialysate discharging line for discharging the dialysate from the dialysate flow route within the dialyzer;
   a drip chamber connected to the venous blood circuit;
   an overflow line extending from an air layer side of the drip chamber for discharging overflowed solution from the drip chamber;
   a valve means being able to arbitrarily open and close the overflow line;
   a venous bubble detecting means arranged at a predetermined portion near the tip of the venous blood circuit for detecting bubbles in the solution flowing through the predetermined portion; and
   a closed circulation circuit being able to be formed by connecting the tip of the arterial blood circuit and the tip of the venous blood circuit when performing the priming operation before the dialysis treatment
   a control means configured and arranged to control the blood pump and the valve means and receive detecting signals from the venous bubble detecting means;
   wherein the control means is configured and arranged to perform sequentially, during the priming operation, steps under a condition in which the blood inlet port of the dialyzer is set at a top position, said steps comprising:
      an overflowing step in which the priming solution is supplied to the drip chamber from the priming solution supplying line via the venous blood circuit and then discharged through the over flow line by stopping the blood pump and opening the valve means;
      a circulating step in which the priming solution is supplied to the arterial blood circuit from the priming solution supplying line via the venous blood circuit and the dialyzer by driving the blood pump in reverse and closing the valve means; and
      a shifting step for shifting the circulating step to the overflowing step so long as the venous bubble detecting means detects bubbles.

2. A blood purification apparatus of claim 1 wherein the control means is configured and arranged to perform repeat the overflowing step and the circulating step until bubbles cannot be detected by the venous bubble detecting means.

3. A blood purification apparatus of claim 1 wherein a drip chamber for the priming solution is arranged on the priming solution supplying line, and wherein the control means is configured and arranged to perform a priming solution pool forming step for forming a priming solution pool within the drip chamber for the priming solution before a first overflowing step.

4. A blood purification apparatus of any claim 1 wherein the control means is configured and arranged to, during the priming operation before the first overflowing step, perform a dialysate charging step in which the dialysate introducing line and the dialysate discharging line are connected respectively to the dialysate inlet port and the dialysate outlet port to pass the dialysate through the dialysate flow route within the dialyzer and to fill it with the dialysate.

5. A blood purification apparatus of claim 1 wherein the control means is configured and arranged to, during the circulating step, reduce the pressure in the dialysate flow route within the dialyzer.

6. A blood purification apparatus of claim 5 further comprising an ultrafiltration pump for ultrafiltrating the blood of a patient flowing in the dialyzer, and wherein the pressure in the dialysate flow route within the blood purification means dialyzer is reduced by driving the ultrafiltration pump.

7. A blood purification apparatus of claim 1 wherein the control means is configured and arranged to, after the overflowing step and before the circulating step, perform the normal rotation of the blood pump.

8. The blood purification apparatus of claim 1 wherein the control means is configured and arranged to, during the circulating step, perform supply of the dialysate to the dialysate flow route within the dialyzer while supplying of the priming solution to the blood flow route within the blood purification means.

9. A method for priming a blood purification apparatus comprising:
- a blood circuit including an arterial blood circuit and a venous blood circuit for extracorporeally circulating the blood of a patient from a tip of the arterial blood circuit to a tip of the venous blood circuit;
- a dialyzer for purifying the blood of a patient flowing through the blood circuit interposed between the arterial blood circuit and the venous blood circuit of the blood circuit and formed with a blood flow route through which the blood of a patient flows and a dialysate flow route through which dialysate flows via blood purification membranes arranged therebetween;
- a blood pump arranged in the arterial blood circuit;
- a dialysate introducing line and a dialysate discharging line connected respectively to an inlet port and an outlet port of the dialysate flow route of the blood purification means;
- a priming solution supplying line connected to the arterial blood circuit for supplying priming solution to the blood circuit;
- a blood inlet port and a blood outlet port arranged at opposite ends of the blood purification means, the blood inlet port being connected to the arterial blood circuit for introducing the blood therefrom into the blood flow route within the dialyzer and the blood outlet port being connected to the venous blood circuit for discharging the blood from the blood flow route within the blood purification means;
- a dialysate inlet port and a dialysate outlet port arranged at the side of the dialyzer, the dialysate inlet port being connected to the dialysate introducing line for introducing the dialysate therefrom into the dialysate flow route within the dialyzer and the dialysate outlet port being connected to the dialysate discharging line for discharging the dialysate from the dialysate flow route within the blood purification means;
- a drip chamber connected to the venous blood circuit;
- an overflow line extending from an air layer side of the drip chamber for discharging overflowed solution from the drip chamber;
- a valve means being able to arbitrarily open and close the overflow line;
- a venous bubble detecting means arranged at a predetermined portion near the tip of the venous blood circuit for detecting bubbles in the solution flowing through the predetermined portion; and
- a closed circulation circuit being able to be formed by connecting the tip of the arterial blood circuit and the tip of the venous blood circuit when performing the priming operation before the dialysis treatment, wherein the following steps are sequentially performed during the priming operation under a condition in which the blood inlet port of the dialyzer is set at a top position, said steps comprising:
- an overflowing step in which the priming solution is supplied to the drip chamber from the priming solution supplying line via the venous blood circuit and then discharged through the over flow line by stopping the blood pump and opening the valve means;
- a circulating step in which the priming solution is supplied to the arterial blood circuit from the priming solution supplying line via the venous blood circuit and the dialyzer by driving the blood pump in reverse and closing the valve means; and
- a shifting step for shifting the circulating step to the overflowing step so long as the venous bubble detecting means detects bubbles.

10. A method for priming a blood purification apparatus of claim 9 wherein the overflowing step and the circulating step are repeated until bubbles cannot be detected by the venous bubble detecting means.

11. A method for priming a blood purification apparatus of claim 9 wherein a drip chamber for the priming solution is arranged on the priming solution supplying line, and wherein a priming solution pool forming step for forming a priming solution pool within the drip chamber for the priming solution is performed before a first overflowing step.

12. A method for priming a blood purification apparatus of claim 9 wherein during the priming operation before the first overflowing step a dialysate charging step is performed in which the dialysate introducing line and the dialysate discharging line are connected respectively to the dialysate inlet port and the dialysate outlet port to pass the dialysate through the dialysate flow route within the dialyzer and to fill it with the dialysate.

13. A method for priming a blood purification apparatus of claim 9 wherein the pressure in the dialysate flow route within the dialyzer is reduced during the circulating step.

14. A method for priming a blood purification apparatus of claim 13 further including an ultrafiltration pump for ultrafiltrating the blood of a patient flowing in the dialyzer, and wherein the pressure in the dialysate flow route within the dialyzer is reduced by driving the ultrafiltration pump.

15. A method for priming a blood purification apparatus of claim 9 wherein the blood pump is driven as the normal rotation after the overflowing step and before the circulating step.

16. A method for priming a blood purification apparatus of claim 9 wherein the dialysate is supplied to the dialysate flow route within the dialyzer while the priming solution is supplied to the blood flow route within the dialyzer during the circulating step.

* * * * *